United States Patent
Bräuer et al.

(10) Patent No.: US 6,373,577 B1
(45) Date of Patent: Apr. 16, 2002

(54) SURFACE PLASMON RESONANCE SENSOR FOR THE SIMULTANEOUS MEASUREMENT OF A PLURALITY OF SAMPLES IN FLUID FORM

(75) Inventors: Andreas Bräuer, Schlöben; Norbert Danz, Jena; Kristina Schmidt; Dirk Vetter, both of Heidelberg; Ralf Waldhäusl, Jena, all of (DE)

(73) Assignees: Graffinity Pharmaceutical Design GmbH, Heidelberg; Fraunhofer Gesellschaft zur Foerderung der angewandten Forschung e.V., Munich, both of (DE)

( * ) Notice: Subject to any disclaimer, the term of this patent is extended or adjusted under 35 U.S.C. 154(b) by 0 days.

(21) Appl. No.: 09/600,670
(22) PCT Filed: May 19, 1999
(86) PCT No.: PCT/EP99/03596
§ 371 Date: Jul. 20, 2000
§ 102(e) Date: Jul. 20, 2000
(87) PCT Pub. No.: WO99/60382
PCT Pub. Date: Nov. 25, 1999

(51) Int. Cl.⁷ .............................. G01N 21/55; G01N 1/10
(52) U.S. Cl. ....................................... 356/445; 356/246
(58) Field of Search ................................ 356/445, 244, 356/246, 446, 448

(56) References Cited

U.S. PATENT DOCUMENTS

| | | | |
|---|---|---|---|
| 4,889,427 A | * 12/1989 | Van Veen et al. | 356/445 |
| 5,164,589 A | * 11/1992 | Sjodin | 250/227.24 |
| 5,779,978 A | 7/1998 | Hartmann et al. | |
| 5,917,607 A | * 6/1999 | Naya | 356/445 |
| 5,923,031 A | * 7/1999 | Naya | 250/227.25 |
| 6,018,388 A | * 1/2000 | Nawracala et al. | 356/246 |
| 6,111,652 A | * 8/2000 | Melendez et al. | 356/445 |

FOREIGN PATENT DOCUMENTS

| | | |
|---|---|---|
| EP | 0343826 | 5/1989 |
| EP | 0793090 | 9/1997 |
| JP | 9-292333 | 11/1997 |
| WO | WO94/16312 | 7/1994 |
| WO | WO95/22754 | 8/1995 |

OTHER PUBLICATIONS

Biosensors & Bioelectronics 9 (1994) pp. 139–146 "Characterization of biomembranes by spectral ellipsometry, surface plasmon resonance and interferometry with regard to biosensor application" by Ch. Striebel, A. Brecht & G. Gauglitz.

Biacore AB, Rapsgatan 7, S–75450 Uppsala, Sweden 1996.

Berger C.E.H. et al.: "Surface Plasmon Resonance Multisensing" Analytical Chemistry, vol. 70, No. 4, Feb. 15, 1998 pp. 703–706, XP000738807.

* cited by examiner

Primary Examiner—Frank G. Font
Assistant Examiner—Michael Stafira
(74) Attorney, Agent, or Firm—Jordan and Hamburg LLP

(57) ABSTRACT

The invention relates to a surface plasmon resonance sensor for the simultaneous measurement of a plurality of samples present in fluid form. The aim of the invention is to provide such a sensor which can be arranged into a defined array and where the surface plasmon resonance sensors can be produced using technology which is simpler and more economical than those produced according to the prior art. To this end several strip-like optical wave guides (2) are arranged on a planar support (1) at a defined distance to each other in such a way that their front faces (21, 22) are flush with opposite sides (11, 12) of the planar support (1). Each strip-like optical wave guide (2) in a section which is to be brought into contact with the fluid samples has at least one thin metal layer (3) which permits the excitation of surface plasmons. Means (14) are provided for which separate the measurement zones of the individual thin metal layers (3) from each other in such a way that each of the optical wave guides (2) can be assigned to only one sample.

14 Claims, 4 Drawing Sheets

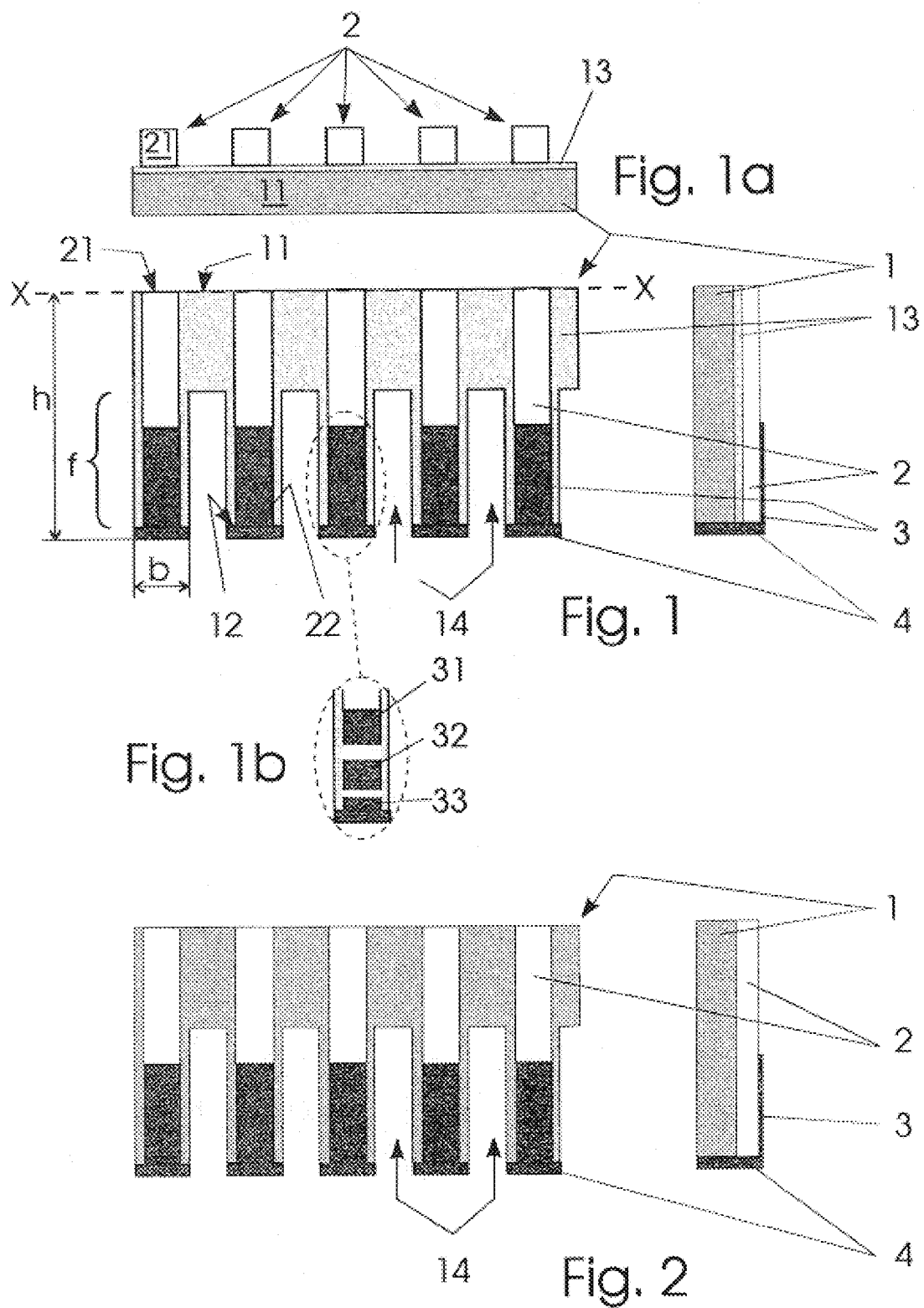

Figure 3A:
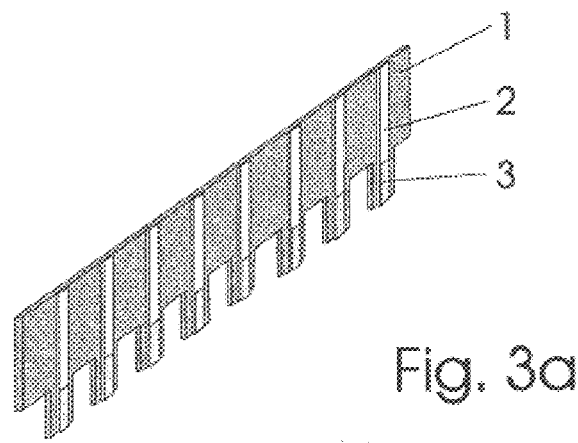

SURFACE PLASMON RESONANCE SENSOR FOR THE SIMULTANEOUS MEASUREMENT OF A PLURALITY OF SAMPLES IN FLUID FORM

BACKGROUND OF THE INVENTION

The invention relates to a surface plasmon resonance sensor for the simultaneous measurement of a plurality of samples present in fluid form that permits a fast sample measurement within the frame of various application purposes. In particular, the sensor according to the present invention is utilized in parallel or serial measurement of samples, which are contained in micro-titer plates.

Due to the more and more expedited automation in the field of search for effective substances, the question of miniaturization and parallelizing finds an increasing interest. The miniaturization of sample receptacles and apparatus for synthesis and the parallelizing of the sequence of procedures leads to a plurality of substances to be tested which are of less and less volume. Thus, when implementing novel detection systems and sensor systems it is necessary to embody the detection systems and sensor systems in such a manner to enable a simultaneous and parallel execution of a plurality of measurements, respectively, a subsequent measurement of a great number of samples within a shortest time, wherein the amount of substances required is minimized. Thereby, the increase of the degree of automation plays an important role.

Background of the invention is the need to provide also the sensors used in measurements in a parallel and miniaturized design so that the measurement of a plurality of samples can be carried out in the shortest possible time and with a minimum of sample volume and expenditures and, thus, to increase the throughput of substances to be identified.

There is known a very sensitive method for specifying the characteristics of boundary faces that, in the references, is referred to as surface plasmon resonance spectroscopy, generally designated as SPR (surface plasmon resonance). This method is based upon the optical excitation of surface plasmons in thin metal layers. According to the state of art, this method has been described, inter alia, in detail by Striebel, Ch.; Brecht, A.; Gauglitz, G. in Biosensors & Bioelectronics 9 (1994), 139–146. The resonance conditions for the excitation of surface plasmons strongly depend on the optical properties of the dielectrics surrounding the metal layer. According to the prior art it is generally feasible with high precision to determine the refractive index and the layer thickness of thin dielectric layers. SPR-spectroscopy finds an increasing use, for example, in the biochemical analysis, since it permits a direct investigation of the interactions between the bio-molecules (for example, antibody/antigen reactions). To this end a reactant (ligand) is immobilized on the metal surface, the other reactant (analyt) is passed over the surface in solution. The interaction can be directly detected as an increase in layer thickness via the refractive index change.

Conventional SPR-sensors (refer to product specification of the firm Biacore AB, Rapsgatan 7, S-75450 Uppsala, Sweden 1996) employ a prism which supports a thin metal layer. The sample to be measured is brought into contact to the metal, respectively, to the modified metal surface, and the SPR-reflection spectrum of the sample is measured by coupling-in light and measuring the intensity of the reflected light as a function of the angle of incidence or of the wavelength.

Recent methods and devices (WO 94/16312) employ fiber-optical elements for setting up SPR-sensors. Thereby commercially available light conducting fibers are used, having a diameter of from 1 $\mu$m to 2000 $\mu$m. The fibers or other defined portions thereof are dismantled, that is, the covering which consists of a wave guide cover and a buffer layer, are removed mechanically or chemically or thermally. Subsequently, the fibers are radially or partially radially provided with a metal layer and, when employing fiber-optical sensor operating as an end-reflector, the leading face of the fiber is additionally coated. Thereby, there are very high standards required from the radial coating as to the homogeneity of the layer thickness that can only be realized technologically under high expenditures.

A further disadvantage when using light conducting fibers lies in the reduced chance for a parallelizing, since single light conducting fibers have always to be arranged manually to obtain an array.

SUMMARY OF THE INVENTION

It is an object of the present invention to provide an SPR-sensor for the simultaneously measurement a plurality of samples present in fluid form that can be arranged to a preselectable array, wherein the SPR-sensors will be manufactured by way of a uniform technology and at less expenditures than involved by those of the prior art.

The object is realized by features of the first patent claim. Preferable embodiments are subject matter of the dependent claims.

The object of the invention is realized by planar waveguides, each of which being provided with at least one SPR-sensor area. SPR-sensor according to the invention can be arranged in parallel and can simultaneously be brought into contact with a great number of samples (greater 100).

The planar waveguides used thereby conduct the excitation light to the sensor area that operates on the measuring principle of the surface plasmon resonance in order to measure a solution brought into contact to the sensor. Thereby exactly one sample is brought into contact with one respective sensor area so that it is feasible to determine n-different samples with one SPR-waveguide array constituted of n-waveguides. One SPR-waveguide array will be manufactured by way of utilizing technologies from the semiconductor production and from the integrated optics to provide in parallel a great number of sensors and to arrange the same at a defined distance to one another.

According to the invention it is also feasible to integrate the SPR-waveguide arrays in sample receptacles, for example, in micro-titer plates. Thereby, the SPR-waveguide arrays are adapted to match with already existing sizes of micro-titer plates (96, 386, 1536 etc.), but also to novel formats or to such ones departing from the already existing formats.

Planar waveguides are increasingly taken notice of in research and development in the field of integrated optics. A light conducting layer is deposited level to a support material when manufacturing planar waveguides. The refractive index of the support material or a layer adapted thereupon to that purpose has to be lower than the refractive index of the waveguiding layer to ensure that the light in the waveguide is guided substantially without any loss. Such planar waveguides are produced by use of known technologies of the semiconductor techniques and integrated optics such as, for example, CVD-processes, sputtering, electron beam vaporization, centrifugation or various replication techniques. It is also feasible to manufacture minutely structurized waveguides and wave branching elements under use of known micro-technological methods of structurizing. Thereby and by use of diverse structurizing methods, waveguides can be produced having a thickness in a range of from a few µ-meters up to some 100 µm and widths up to some 1000 µm. The coating of defined waveguide sections with a layer capable of SPR can also be carried out in parallel with a few steps by known technologies.

An SPR-sensor according to the present invention is comprised of a plurality of planar stripe-shaped light wave guides that are provided, between respective two leading faces, with at least one two-dimensional measuring area. These measuring areas are coated with a planar metal layer capable of SPR that is in direct contact with both, the waveguiding material and the sample to be determined.

The excitation light enters the light wave guide via known coupling mechanisms. There the light propagates in and along the waveguide and is guided to the sensor area. In the sensor area the light guided in the light wave guide is affected by excitation of the surface plasmons.

In the further course, the modified light is either coupled-off from the light wave guide by way of the known coupling principles directly after passing the sensor area and is passed on to further processing; or it is back-reflected in itself in the light wave guide by means of a mirror coating deposited on the leading face and is coupled-off again via the same coupling mechanism by which the light entered into the light wave guide, and is thus provided for further processing.

When the light is coupled-in and coupled-out at one and the same side of the light wave guide and the reflection of the radiation takes place at the other end, then planar SPR-waveguides on the basis of end-reflection are concerned. When the coupled-in light leaves the waveguide at the second side of the waveguide then one speaks of waveguide sensors based on inline-transmission.

DETAILED DESCRIPTION OF THE INVENTION

Figure 3B:
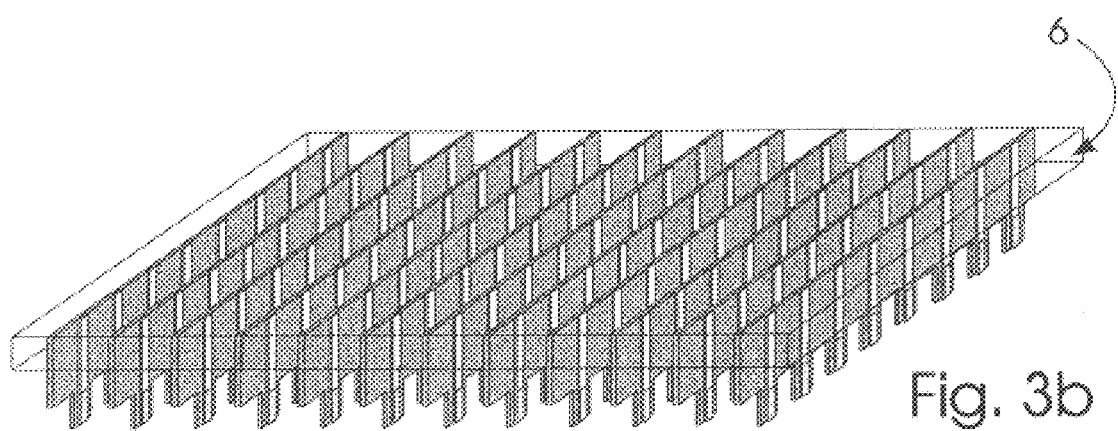
Figure 4:
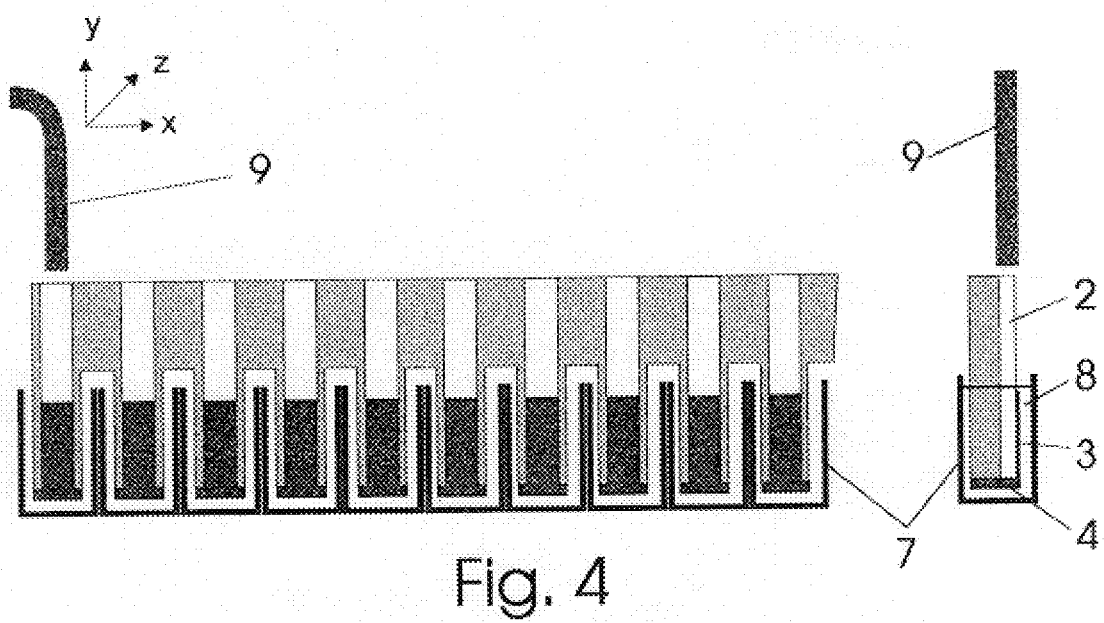

The invention will be explained in more detail by virtue of the following schematical embodiments. There is shown in:

FIG. 1 a first embodiment of a one-dimensional SPR-sensor capable of being set up into an array, FIG. 1a a plan view of an SPR-sensor of FIG. 1, shown in a plane X—X, FIG. 1b a partial view of FIG. 1, FIG. 2 a second embodiment of an SPR-sensor embodied substantially in analogy to FIG. 1, FIG. 3a a perspective view of an SPR-sensor according to FIG. 1 or FIG. 2, FIG. 3b an arrangement of a plurality of SPR-sensors according to FIG. 3a adapted to form an array, FIG. 4 a sectional view of an embodiment for inserting an SPR-sensor array of comb-like design, comprised of planar SPR-sensors according to FIG. 1 or 2 into a micro-titer plate.

Figure 5:
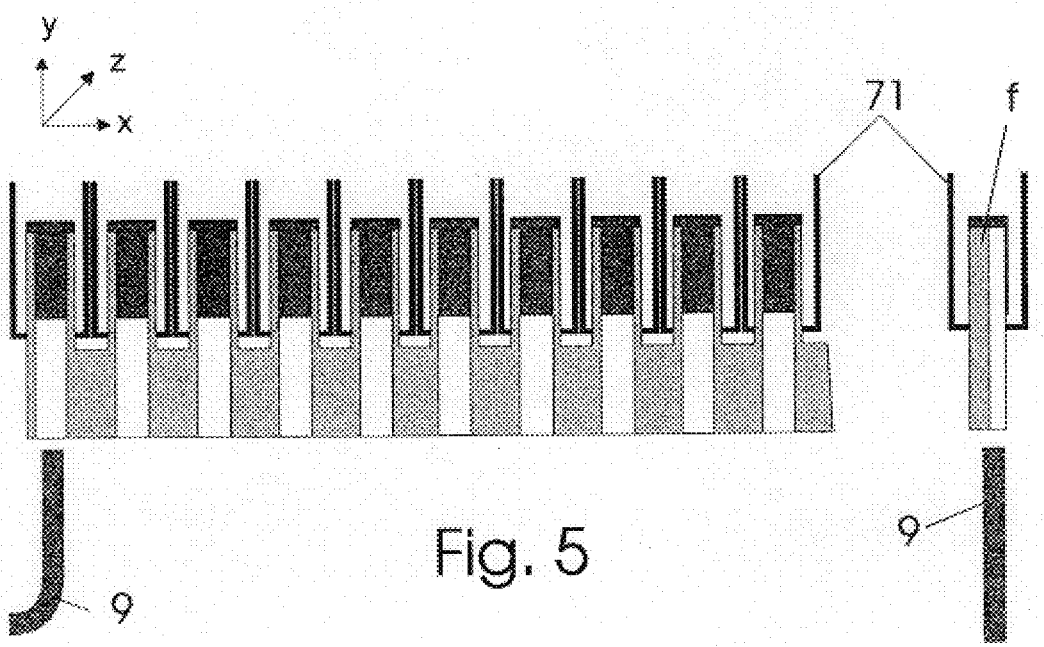

FIG. 5 an embodiment of an arrangement of SPR-sensors, the mutual space between adjacent ones is constituted by cell walls.

Figures 6A, 6B:
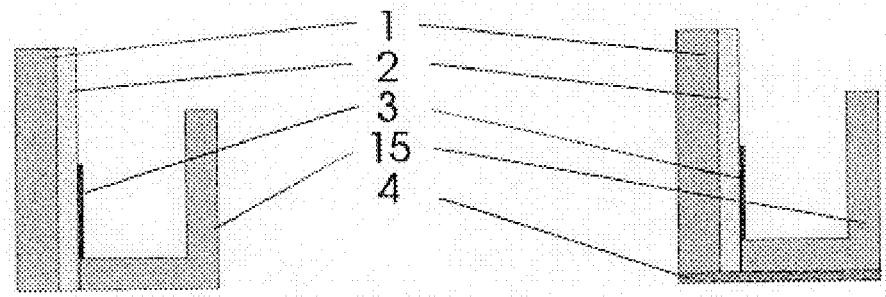
Figure 6C:
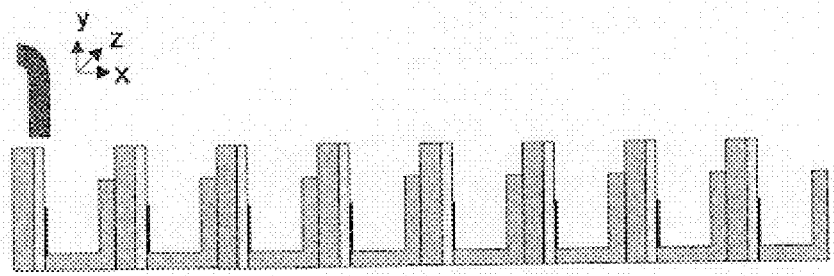
Figure 7:
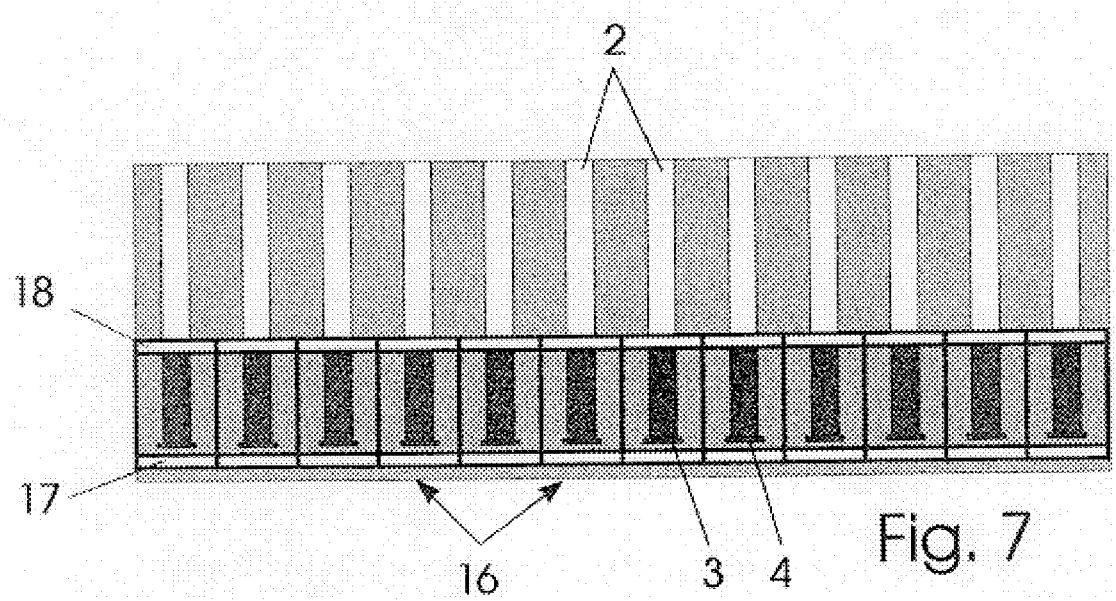

FIG. 6a an embodiment of an SPR-sensor in which each single sensor is additionally bordered by cell walls, FIG. 6b a further embodiment of an SPR-sensor array according to FIG. 6a, FIG. 6c multiple arrangement of an embodiment according to FIG. 6a, and FIG. 7 a further embodiment according to FIG. 6b.

In FIG. 1 in a first embodiment a partial section of an SPR-sensor is shown. Therein, a plurality of strip-shaped light wave conductors 2 mutually arranged at defined distances are provided on a planar base 1 in such a way that the leading faces 21, 22 are flush with the respective sides 11, 12 of the planar base 1. Thereby each of the strip-shaped light wave conductors 2 is provided in a section of said conductors with a thin metal layer 3 which permits the excitation of surface plasmons, said section being adapted to be brought into contact with fluid samples to be analyzed, not shown in FIG. 1. In the example according to FIG. 1, the starting point is a 4"-silicon wafer used in the semiconductor techniques into which initially the structures of a plurality of planar bases 1 have been transferred and structurized. Thereby long and narrow rectangular apertures are structurized in the wafer, said apertures forming the comb-shaped recesses 14 after separation shown in FIG. 1. A mask which, in the example, is used to this end has to be shaped to such a geometry that the resulting comb-shaped structures, after having been separated, can be submerged in micro-titer plates of a 1536 format (32×48 cavities). It is evident that only a section thereof is shown in FIG. 1. In order to ensure a strength as high as possible for the single bases 1, a silicon wafer has been selected having a crystal orientation (110) that permits to structurize rectangular spaces with right angular edges at least at two edges. Subsequently, the structurized wafer of the example is coated with $SiO_2$ by way of a PE-CVD process. This $SiO_2$-layer is adapted as an optical buffer between the arranged light wave conductors 2 and the Si-substrate.

The light wave conductors according to FIG. 1 consist of a siliconoxynitride layer of, for example, a thickness of about 10 µm. The light wave conductors 2 are shaped, according to the scope of the present invention, by a conventional dry etching procedure of the siliconoxynitride layer in such a way that parallel stripes result having a width of between 10 µm to 2000 µm and distances between 10 µm and 5000 µm.

Furthermore, it is feasible within the scope of the invention to vary the last mentioned sequence of structurizing in such a way that, on a non-structurized Si-wafer, initially all the coatings mentioned are applied to the entire surface of the wafer and, subsequently thereto, the comb-shaped structure as shown in FIG. 1 is produced by employing the known selective structurizing procedures. In FIG. 1a there is shown a plan view of the structures, obtained in the above manner, along the plane X—X of FIG. 1.

Furthermore, it lies within the scope of the invention to manufacture the light wave conductor 2 of a polymer that can be hardened by the effect of UV-light. To this end a liquid polymer, for example, PMMA, polycarbonate, IV-hardened adhesives or silico-polymers (cyclotene or ORMOCERE) is sputtered upon the wafer or embedded by casting on the same. The structurizing of the light wave conductor is performed by known photolithographic methods under use of a respectively prepared mask. The exposed areas are cross-linked and hardened by UV-radiation, whereas the unexposed areas are removed while developed so that the exposed areas remain as light wave conductors 2.

The light wave conductor 2, in the most cases, has to be designed of square cross-section, whereby departures due to manufacturing conditions may occur. The cross-section in the example according to FIG. 2 is about 190 µm×190 µm, the width b of the fingers f is about 550–600 µm, whereby the light wave conductors 2 have to be centrally arranged on the fingers f.

Such a dimensioning ensures an adaptation as far as possible to the light conducting fibers, which will be referred to in more detail in the following, of the presently used diameters of 200 µm. The length of the sections comprising the fingers f is 5 mm in the example.

Under the condition that the optical refractive number of the base 1 material is lower than the refractive number of the polymer to be deposited, and that said material is not absorbing, the present example according to FIG. 2 can do without an additional and prior application of an optical buffer layer 13, as required in FIG. 1.

There can also be used different polymers that, for example, are brought into the desired stripe shape by embossing or any other replication techniques, whereby the thickness of the remaining material has to lie under the critical cut-off-thickness in those parts in which no light has to be conducted.

Subsequent to the above described structurizing of the strip-shaped light wave conductors, the entire wafer in the two embodiments described up to here is protected by a cover coat except for those areas that are to support the metal layer 3 capable of SPR. Thereafter, these uncovered areas are coated with the metal sheet capable of SPR, for example, with a thin gold layer by sputtering, and subsequent thereto the protective coat is removed from the remaining covered areas.

Preferably the structures for the SPR-sensors on the wafers are produced in such way that the comb-shaped structures are in mirror opposition to one another before being separated. Before starting a subsequent sawing process for separating the comb-structures and in order to protect the light wave conductors 2 against fragments or the like, it is necessary to passivate the light wave conductors 2 provided with the thin metal layers 3 adapted for exciting the surface plasmons.

To this end a thick protective coating is applied. Then a separation process follows, for example, by sawing, so that the desired comb-structures are obtained and the leading faces 21, 22 are produced, said leading faces 21, 22 being adapted to couple-in and couple-out, respectively, light.

Depending on which technology is being used for providing the desired comb-shaped recesses in the base body 1, said recesses 14 can be manufactured before or after the application of said metal layer 3.

In the examples according to FIGS. 1 and 2, said application is carried out subsequently at least on those areas of the light wave conductor 2 that are formed by the leading faces 22 in the range of the metal layer 3. The application of the reflecting coat 4 can be achieved, for example, by a new coating process, for example, by sputtering of an aluminum layer or a silver layer. To this end and before the separation process, the wafer is provided with a protective coat over its entire surface, said protective coat ensuring that the structures 2, 3 that have been applied before, are not contaminated during the end portions are being mirror coated. The protective coat is removed after mirror coating.

In the examples according to FIGS. 1 and 2, the single SPR-sensor areas that are formed by the metal layers 3 are separated from one another by the comb-shaped recesses 14. Thus and, for example, by immersion into an arrangement of complementarily distributed receptacles of a micro-titer plate, each of the light wave conductors 2 can be associated to only one sample.

In FIG. 3a a perspective view of an SPR-sensor according to FIGS. 1 or 2 is shown. In order to implement an array of sensors, a plurality of such stripes are placed in a serially stacked arrangement. Offside the ranges that are provided with a thin metal layer 3 enabling the excitation of the surface plasmons, the stripes are held by a common holding means and are spaced apart in such a manner that their space corresponds, for example, to the space between the receptacles of a micro-titer plate format preselectable at will. In this way arrays of SPR-sensors, adaptable as desired, for example, 8×12 as shown in FIG. 3b, can be manufactured. After assembly, such an array is advantageously embedded in a polymeric casting by that area which is not provided with the metal layer 3 capable of SPR, in order to give an additional support to the SPR waveguide array, as indicated schematically in FIG. 3b by a polymeric sealing block 6. For performing measurements, said SPR waveguide array is brought into contact to a micro-titer plate that supports the samples to be analyzed. Thereby, in order to obtain an optimal measurement, the SPR waveguide array is inserted into the micro-titer plate 7 so far until the metal areas 3 capable of SPR are completely wetted by a sample 8, as schematically shown in FIG. 4.

A further feasible arrangement of the SPR-sensors is indicated in FIG. 5. In this example the single SPR-sensors are spaced apart from one another by the cell walls 71 which comprise a respective finger f of the mentioned comb-structure. In this example an SPR-array according to the principle of end-reflection is employed.

Furthermore, in the examples according to FIGS. 4 and 5, an external light conducting fiber 9 is shown that can be accurately positioned over the respective leading faces of the light wave conductor 2 by use of an x,y-displacement table.

Thereby, this light conducting fiber (9) couples-in light from a white light radiation source (not shown in detail) into the respective light wave conductor 2, and this light being passed to the excitation area of the surface plasmons where it is subsequently reflected at the second mirror-coated leading face. After the guided light has passed the excitation area for a second time after reflection, the light from the light wave conductor 2 is coupled-out via the leading face and passed into the common branch of a not shown fiber branching element. From there, the light arrives in, for example, a spectrometer (not shown) for spectral evaluation. The spectrometer control and the data collection is carried out computer controlled by a PC.

Alternatively, the spectrum can be determined in that the SPR-array is measured in transmission. Instead of the fiber branching element a simple light conducting fiber 9 is used for coupling-in the light into the light wave conductor 2. A second light conducting fiber is positioned at the exit of the light wave conductor 2. Said second light conducting fiber conducts the light to a diffraction-grating spectrometer. Such a configuration can do without a mirror coating on the end face of the light wave conductor 2. However, the interaction length, i. e. the effective sensor length, is reduced by 50%. The signal is less distinct by that factor. On the other hand, two coupling sites have to be positioned so that the expenditures for apparatus and adjustment are increased.

Depending on the used measuring and computing technique, it is also feasible to associate a light conducting fiber 9 to each of the provided light wave conductors 2, thereby enabling a simultaneous evaluation of all samples present.

Two further embodiments, illustrated in FIGS. 6a and 6b are designed in a way that the means separating the detection ranges of the single thin metal layers 3 from one another are constituted by cell walls 15 connected to the planar base 1. Also in these embodiments both above mentioned operation modes are possible. Thus, an embodiment according to FIG. 6a is adapted for an in-line operation, whereas an embodiment according to FIG. 6b for the reflection mode operation by providing a mirror-coating 4.

In FIG. 6c there is indicated how an SPR-sensor array can be manufactured by a multiple arrangement similar to the stacked arrangement, described in FIG. 3b, of single lines supporting a plurality of SPR-sensors according to FIG. 6a.

The invention is not restricted to the represented examples. In general, it is essential that the planar bases 1 are used that are provided with substantially plane light wave conductors exhibiting, in a sample detection area, at least one respective metal layer 3 capable of SPR that constitutes one respective sample detection area which can be brought into contact with a sample. It also lies within the scope of the invention to establish a communication between the areas capable of SPR and the open bottoms of mutually spaced flow cells 16, FIG. 7, which have a common inflow 17 and a common outflow 18. In particular, in such an embodiment at least one of the provided flow cells can be used as reference channels, for example, to compensate for temperature variations.

When within the frame of the invention there is reference to at least one two-dimensional measuring area, then thereby is to be understood that the metal layer 3 provided as a sensor area can be subdivided into a plurality of partial areas 31, 31, 33, as indicated in FIG. 1b.

Furthermore, the inventional SPR-sensor can be employed in such a way that initially one single sample is immobilized in the sensor areas 3. This immobilization is adapted to prepare a chemically modified measuring surface, and a further sample, preferably in solution, can enter into interaction with said chemically modified surface. In the case of the immobilized sample, this is frequently referred to as ligand, whereby the sample in solution is very often called receptor or analyt. Thus, the interaction partners are, for example, ligand-receptor is couples. Then, an SPR-sensor according to the present example enables the simultaneous measuring of a plurality of different samples (analyts).

All features disclosed in the specification, in the subsequent claims, and in the drawing are substantial for the invention both, individually and in any combination with one another.

List of Reference Numerals

1—planar base
11, 12—(opposing) sides (of the planar base 1)
13—buffer layer (coating)
14—recesses
15—cell walls
16—flow cells
17—inflow
18—outflow
2—light wave conductor
21, 22—leading faces of the light wave conductor 2
3—metal layer capable of SPR
31, 32, 33—partial areas of the metal layer 3
4—light-reflecting coat
6—sealing block
8—sample
9—light conducting fiber
b—width of the fingers f
f—fingers
h—length of fingers f
X—X—plane

What is claimed is:

1. SPR-sensor for the simultaneous measurement of a plurality of samples present in fluid form, characterized in that a plurality of strip-shaped light wave conductors (2) mutually arranged at a defined distance are provided on a planar base (1) in such a way that they via their leading faces (21, 22) are flush with oppositely arranged sides (11, 12) of the planar base (1); whereby each of the strip-shaped light wave conductors (2) is provided in a section thereof with at least one thin metal layer (3) enabling the excitation of surface plasmons, said section being adapted to be brought into contact with fluid samples, and in that means are provided (14, 15) that separate the detection areas of the single thin metal layers (3) in such a way that each light wave conductor (2) is associable to only one sample.

2. SPR-sensor as claimed in claim 1, characterized in that the strip-shaped light wave conductor (2) is substantially given a square cross-section.

3. SPR-sensor as claimed in claim 2, characterized in that the level extensions of the cross-section of the strip-shaped light wave conductor (2) matches the level extensions of the cross-section of the light conducting cores of conventional light conducting fibers (9).

4. SPR-sensor as claimed in claim 1 or 2, characterized in that a leading face (22) of the strip-shaped light wave conductors (2) located in the range of the samples is provided with a light-reflecting coat (4).

5. SPR-sensor as claimed in claim 1, characterized in that means for separating the detection areas of the single thin metal layers (3) from one another are in the shape of comb-shaped recesses (14) formed in the planar base (1).

6. SPR-sensor as claimed in claim 1, characterized in that said means for separating the detection areas of the single thin metal layers (3) from one another are formed by cell-walls (15) connected to the planar base (1).

7. SPR-sensor as claimed in claim 1, characterized in that the planar base (1) is made of silicon and is provided with a coating (13), for example, of $SiO_2$ at least below the strip-shaped light wave conductors (2), the optical refractive index of said coating being lower than the optical refractive index of the material, for example, siliconoxynitride, which is used for the strip-shaped light wave conductor (2).

8. SPR-sensor as claimed in claim 1 or 7, characterized in that a silicon wafer having a crystal orientation (110) is selected for the planar base (1).

9. SPR-sensor as claimed in claim 1, characterized in that the planar base (1) is made of a material, the optical refractive index of which is lower than the optical refractive index of the material, for example, a polymer, which is used for the strip-shaped light wave conductor (2).

10. SPR-sensor as claimed in claim 6, characterized in that the cell walls (16) separating the detection areas of the single thin metal layers (3) from one another, are connected with one another via a common inflow (17) and outflow (18).

11. SPR-sensor as claimed in any one of claims 1 to 3, 5 to 7, and 9 and 10 characterized in that the fingers (f) of the planar base (1) are adapted to be received by respective receptacles (8) of a micro-titer plate (7), whereby the strip-shaped light wave conductors (2) with their thin metal layers (3) enabling the excitation of surface plasmons are supported by said planar base.

12. SPR-sensor as claimed in claim 11, characterized in that the strip-shaped light wave conductors (2) with their thin metal layers (3) enabling the excitation of the surface plasmons and, where appropriate, with a light wave conductor (2) provided with a reflective coating (4) on the leading face, are provided at a respective wall of a receptacle of a micro-titer plate (7), whereby a respective layer having a lower optical refractive index than the light wave conductor is arranged in-between.

13. SPR-sensor as claimed in any one of claims 1 to 3, 5 to 7, 9 and 10 characterized in that a plurality of planar bases (1) supporting the strip-shaped light wave conductors (2) and the remaining mentioned units (3 and, if any, 13, 4) are held, offside the ranges that are provided with a thin metal layer (3) enabling the excitation of the surface plasmons, by a common holding means and are spaced apart in such a manner that their spaces correspond to the spaces of the receptacles of a micro-titer plate format preselectable at will.

14. SPR-sensor as claimed in claim 13, characterized in that the common holding means is a sealing (6) which does not optically affect the light wave conducting properties of the strip-shaped light wave conductor (2) and of the first leading face (21).

* * * * *